Figure 1:
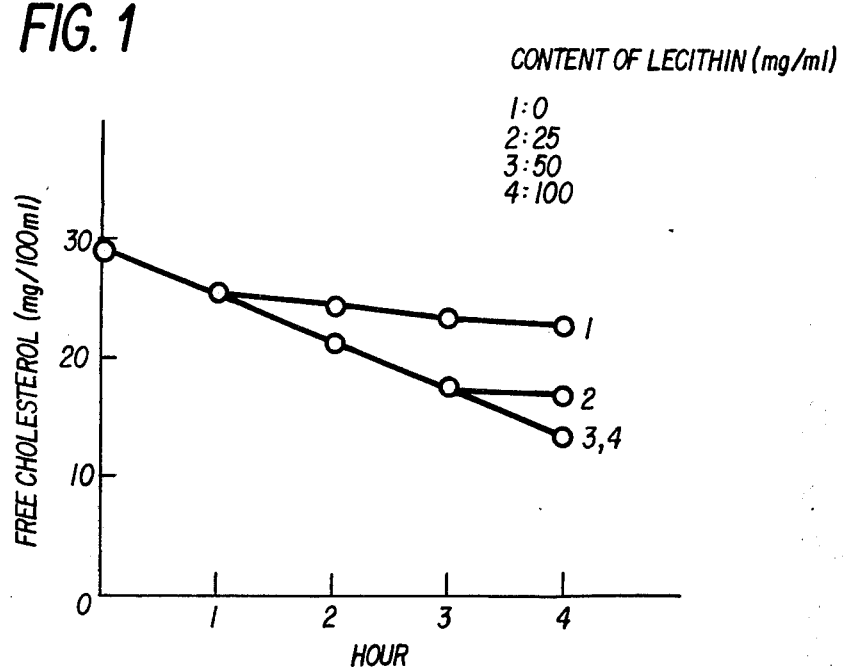

United States Patent [19]

Nagasaki et al.

[11] 4,007,091
[45] Feb. 8, 1977

[54] METHOD FOR MEASURING THE ACTIVITY OF LECITHIN CHOLESTEROL ACYL TRANSFERASE AND LECITHIN SUBSTRATE SOLUTION USEFUL THEREFOR

[75] Inventors: Toshihide Nagasaki, Takarazuka; Masaharu Takayama, Osaka; Akiyoshi Uesugi, Toyonaka; Isao Tanimizu, Ibaraki; Kazuto Shintani, Toyonaka, all of Japan

[73] Assignee: Nippon Shoji Kaisha, Limited, Osaka, Japan

[22] Filed: Apr. 29, 1976

[21] Appl. No.: 681,410

[30] Foreign Application Priority Data

May 2, 1975   Japan .............................. 50-53655

[52] U.S. Cl. ........................... 195/99; 195/103.5 R
[51] Int. Cl.² ....................................... G01N 31/14
[58] Field of Search ..................... 195/103.5 R, 99

[56] References Cited
OTHER PUBLICATIONS

Clinica Chimica Acta, 43:23–26, (1973).

*Primary Examiner*—Alvin E. Tanenholtz
*Attorney, Agent, or Firm*—Stevens, Davis, Miller & Mosher

[57] ABSTRACT

A method for measuring the activity of lecithin cholesterol acyl transferase (LCAT) comprising adding a test sample (a blood serum or plasma) to a lecithin substrate solution containing a lecithin and a nonionic surfactant, incubating the mixture and then measuring the changed amount of the free cholesterol in the reaction system by an optical analysis, and the lecithin substrate solution useful therefor. The method of the present invention is useful for the clinical test for the liver function of patients and further for the diagnosis of the diseases, such as lipidosis and diabetes.

10 Claims, 2 Drawing Figures

METHOD FOR MEASURING THE ACTIVITY OF LECITHIN CHOLESTEROL ACYL TRANSFERASE AND LECITHIN SUBSTRATE SOLUTION USEFUL THEREFOR

The present invention relates to a method for measuring the activity of lecithin cholesterol acyl transferase (hereinafter, referred to as "LCAT") and a lecithin substrate solution useful therefor.

LCAT is an enzyme which is produced in liver of animals and can convert a free cholesterol or lecithin into a cholesterol ester or lysolecithin respectively in blood. The activity of LCAT has a closed relation with the degree of lesion of hepatic cells. For instance, in the patients having an acute hepatitis, the activity of LCAT is lowered, and in the most patients having a chronic hepatitis, the activity thereof is in a nomal value. Besides, more than half of the patients having a hepatocirrhosis show a lower value of the activity, and in the patients having an obstructive jaundice, the activity is lowered with the turn of the disease for the worse. Accordingly, the measurement of the activity of LCAT is useful for the clinical test of the liver function of patients.

Moreover, the activity of LCAT has also a closed relation with the amount of the free cholesterol in blood and further with the degree of fat body (obesity). Accordingly, the measurement of the activity of LCAT is also useful for the diagnosis of the diseases, such as lipidosis and diabetes.

Generally, the activity of an enzyme can be shown by the reaction speed, i.e. by the changed amount of the substrate or the product per a fixed period when a prescribed amount of a test sample containing the enzyme is incubated under fixed conditions. For instance, in case of the measurement of the activity of LCAT, a blood serum or plasma is incubated at 37° C, which is the optimum temperature for the cultivation of LCAT, and then the changed amount ($\mu g$ or $\mu M$) of the free cholesterol (substrate) is measured. The activity of LCAT is represented by the changed amount of the free cholesterol per 1 ml (or 1 liter) of the blood serum per one hour ($\mu g/ml/hour$ or $\mu M/l/hour$).

The reaction speed is decreased with the decrease of the amount of the substrate in the reaction system owing to the enzymatic reaction. In an enzymatic reaction, when a curve of the amount of substrate-the incubation time is described by plotting the amount of the substrate in the reaction system during the incubation period, the curve is usually an approximately linear line only at the first stage of the reaction, and therefore the activity of the enzyme is usually represented by the reaction speed at the first stage of the reaction. However, in case of LCAT, when the curve is described when the test sample is incubated at 37° C, the curve is approximately linear only within one hour from the initiation of the reaction. Accordingly, the incubation time should be shortened for keeping the linear line. In such a short reaction time, the changed amount of the substrate is so small that the changed amount can not be correctly measured by a conventional method, wherein the free cholesterol is measured by an optical analysis.

For measuring the activity of LCAT, there have also been proposed Stokke-Norum method [K. T. Stokke and K. R. Norum, Scand. J. Clin. Lab. Invest., Vol. 27, page 21 (1971)] and a common substrate method [J. A. Glomset and J. L. Wright, Biochim. Biophys. Acta, Vol. 89, page 266 (1964)], wherein a radioisotope is used. However, in these methods, the operation is so complicated, a long incubation time (5 to 6 hours) is required and a radioisotope must be used, and therefore, these methods are hardly used in the clinical test.

The present inventors have extensively studied to fine an improved method for measuring the activity of LCAT suitable for the clinical test without using a radioisotope, i.e. by measuring the free cholesterol by an optical analysis. As the result, it has been found that the reaction time, wherein the curve of the amount of substrate-the incubation time can be kept in an approximately linear line, can be prolonged by incorporating a lecithin into the reaction mixture and that the turbidity of the reaction system owing to the addition of the lecithin can be prevented by adding a surfactant, particularly a nonionic surfactant, together with the lecithin, by which the conventional optical analysis method can be applied to the measurement of the activity of LCAT.

An object of the present invention is to provide an improved method for measuring the activity of LCAT useful for the clinical test of the liver function of patients and for the diagnosis of the diseases, such as lipidosis and diabetes.

Another object of the invention is to provide a lecithin substrate solution containing a lecithin and a surfactant, which is useful for the measurement of the activity of LCAT.

A further object of the invention is to provides a transparent or semi-transparent lecithin substrate solution.

A still further object of the invention is to provide a method for prolonging the reaction time, wherein the curve of the amount of substrate-the incubation time can be kept in an approximately linear line.

These and other objects of the invention will be apparent from the following description.

The measurement of the activity of LCAT of the present invention can be carried out by adding a transparent or semi-transparent lecithin substrate solution, which is prepared by dissolving or dispersing a lecithin and a nonionic surfactant in a buffer solution, to a test sample (e.g. a blood serum or plasma), incubating the test sample incorporated with the lecithin substrate solution, and then measuring the changed amount of the free cholesterol in the reaction system by an optical analysis.

The present inventors have assumed that the linearity of the curve of the amount of substrate-the incubation time in the enzymatic reaction may be prolonged by adding to the test sample a lecithin which is a substrate for LCAT and have plotted the curve of the amount of substrate-the incubation time by adding various concentrations of the lecithin to the test sample. That is, some substrate solutions having various concentrations of the lecithin are prepared by adding the lecithin to a buffer solution (pH 7.4), and a prescribed amount of the substrate solution is added to a prescribed amount of the test sample and the mixture is incubated at 37° C for 4 hours, and then the free cholesterol in the reaction system is extracted and the changed amount thereof is plotted in a graph. The results are shown in the accompanying FIG. 1.

As is made clear from the results, in case no lecithin is added, the linearity of the curve is lost within one hour, but on the other hand, in case a lecithin is added, the linearity of the curve can be kept for 3 hours (the content of the lecithin in the substrate solution: 2.5 mg/ml) and for 4 hours (the content of the lecithin in the substrate solution: 5 or 10 mg/ml), and the addition of the lecithin does not affect on the activity of LCAT. Thus, the linearity of the curve of the amount of substrate-the incubation time can be kept for 2 to 4 hours by adding the lecithin substrate solution containing 2.5 to 10 mg/ml of the lecithin, and the changed amount of the free cholesterol can be precisely measured by a conventional optical analysis method.

When the lecithin alone is added to the buffer solution, the mixture becomes turbid, and when the mixture of the test sample and the substrate solution thus obtained is incubated, it is difficult to measure the changed amount of the free cholesterol by an optical analysis. Accordingly, it is required to make the substrate solution transparent for the purpose of using the method for the clinical test.

It is known that an ultrasonic treatment is useful for the solubilization of a mixture. When a mixture of a lecithin in a buffer solution is treated with an ultrasonic, the turbidity thereof can be somewhat decreased, but some precipitations occur within a few hours. Thus, the substrate solution must be treated with an ultrasonic every when used, and therefore, is not suitable for the clinical test. The present inventors have extensively studied on various solubilizing methods and have found that nonionic surfactants are useful for making transparent or solubilizing the lecithin substrate solution without any undesirable effect on the activity of LCAT.

Figure 2:
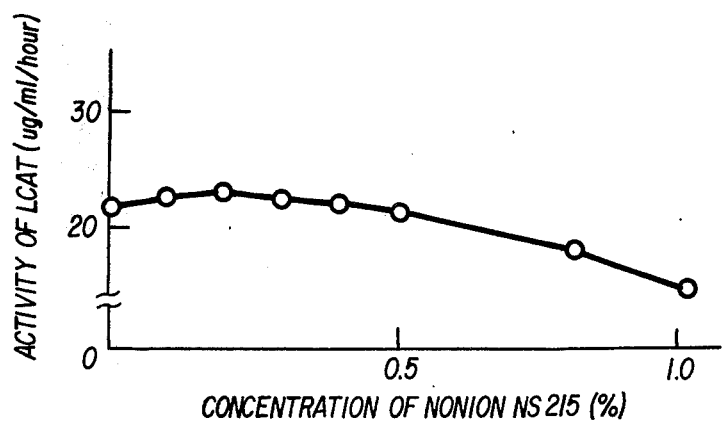

For instance, the relationship between the concentration of Nonion NS 215 (a trade name of a polyoxyethylene alkyl($C_9$) phenol ether, made by Nippon Oils and Fats Co., Ltd.) and the activity of LCAT ($\mu$g/ml/hour) is shown in the accompanying FIG. 2.

As is made clear from FIG. 2, the activity of LCAT is not affected by the nonionic surfactant below 0.5% (W/V) in concentration thereof. Moreover, the nonionic surfactant can make the lecithin substrate solution transparent by adding in an amount of 0.01% (W/V) or more, and when the substrate solution is previously treated with an ultrasonic, it is more readily made transparent or solubilized by the addition of the nonionic surfactant.

Thus, the present invention provides a method for measuring the activity of LCAT by adding a lecithin substrate solution (hereinafter, optionally referred to as merely "lecithin substrate"), which is prepared by adding a lecithin and a nonionic surfactant to a buffer solution, to a test sample, incubating the mixture and then measuring the changed amount of the free cholesterol by an optical analysis method.

The nonionic surfactants used in the present invention include any conventional nonionic surfactants which can make the lecithin substrate transparent and does not give any undesirable effect on the activity of LCAT, such as polyoxyethylene alkyl ethers, polyoxyethylene alkyl phenol ethers, polyoxyethylene sorbitan alkyl esters, polyoxyethylene alkyl esters, polyoxyethylene alkyl amines, polyoxyethylene alkyl amides and sorbitan alkyl esters. Among these surfactants, preferred surfactants are polyoxyethylene alkyl ethers, polyoxyethylene alkyl phenol ethers and polyoxyethylene sorbitan alkyl esters. Suitable examples of the nonionic surfactants are Triton X-100 (a trade name of a polyoxyethylene isooctyl phenyl ether, made by Rohm and Haas Co.), Emulgen 930 (a trade name of a polyoxyethylene alkyl ether, made by Kao Soap), Tween 20 and Tween 80 (trade names of a polyoxyethylene sorbitan monolaurate and a polyoxyethylene sorbitan monooleate respectively, made by Atlas Powder Co.), Nonion NS 215 (a trade name of a polyoxyethylene alkyl ($C_9$) phenol ether, made by Nippon Oils and Fats Co., Ltd.), or the like.

These nonionic surfactants are used alone or in a mixture of two or more kinds thereof in an amount of 0.01% (W/V) or more, preferably 0.02 to 0.5% (W/V), on the basis of the lecithin substrate. However, the nonionic surfactant affects on the activity of LCAT as shown in FIG. 2, while it is slight, and therefore, the nonionic surfactant is preferably used in an amount as small as possible, and the most preferable amount is about 0.025% (W/V).

The lecithin is used in an amount of 2.5 to 10 mg/ml, preferably 2.5 to 5 mg/ml.

The buffer solution used in the present invention may be aqueous buffer solutions which can keep the lecithin substrate at an optimum pH value of LCAT (i.e. pH about 7.4), and includes TEN buffer solution (Tris, i.e. tris(hydroxymethyl)aminomethane: 0.01 M, EDTA, i.e. disodium ethylenediaminetetraacetate: 0.001 M, and sodium chloride: 0.14 M), TE buffer solution (Tris: 0.02 M, and EDTA: 0.001 M), 0.1 M phosphate buffer solution and 0.02 M Tris buffer solution. When the nonionic surfactant is used in a smaller amount, the TE buffer solution is preferable.

The lecithin substrate can be prepared by adding 2.5 to 10 mg/ml of a lecithin to a buffer solution, and preferably treating the resulting mixture with an ultrasonic, and then adding thereto a nonionic surfactant in an amount of 0.01% (W/V) or more, preferably 0.02 to 0.5% (W/V), on the basis of the lecithin substrate solution.

The activity of LCAT can be measured and calculated by using the lecithin substrate thus prepared as follows:

A prescribed amount of a test sample is added to a prescribed amount of the lecithin substrate and the mixture is incubated at 37° C for 3 to 4 hours. The amount of the free cholesterol in the reaction system before and after the incubation is measured by a conventional optical analysis method using a combination of digitonin and a reagent selected from Liebermann-Burchard reagent [cf. W. M. Sperry and M. Webb, J. Biol. Chem., Vol. 187, page 97 (1950)], Zak-Henly reagent [cf. B. Zak and R. C. Dickenman, Am. J. Clin. Path., Vol. 24, page 1307 (1954)] or an o-phthalaldehyde reagent [cf. A. Zlatkis and B. Zak, Anal. Biochem., Vol. 29, page 143 (1969)], or by a cholesterol oxidase method [cf. W. Richmond et al, Clin. Chem., Vol. 19, page 1350 (1973)], and then the difference of the amounts of the free cholesterol before and after the incubation is divided by the incubation time to give the activity of LCAT.

For instance, a test sample (a blood serum or plasma, each 0.5 ml) is added to two test tubes A and B and thereto is added a lecithin substrate (each 0.1 ml). The test tube A is kept in a refrigerator, or after a LCAT inhibitor (e.g. cholic acid, or an alkali metal salt thereof) is added thereto, the test tube A is allowed to stand at room temperature. The test tube B is incubated at 37° C for 3 hours. The content (each 0.1 ml) of the test tubes A and B is taken out therefrom and thereto is added a reagent for measuring the free cholesterol (3 ml, contents: cholesterol oxidase, peroxidase, phenol and 4-aminoantipyrine) [cf. W. Richmond, Clin. Chem., Vol. 20, page 470 (1974)]. The mixture is heated at 37° C for 30 minutes, and the optical density at 500 nm of the resulting mixture is measured. Separately, the optical density of the standard solution containing a constant concentration of the free cholesterol is measured, likewise. On the basis of the values thus measured, the activity of LCAT is calculated by the following equation.

$$U = \frac{(E_A - E_B)}{E_S} \times D \times \frac{1}{T} \times 10 \times 1.2 \quad [I]$$

wherein
- $U$: Unit of the activity of LCAT (μg/ml/hour)
- $E_A$: The optical density of the test sample in the test tube A
- $E_B$: The optical density of the test sample in the test tube B
- $E_S$: The optical density of the standard solution
- $D$: The concentration of the free cholesterol of the standard solution (mg/100 ml)
- $T$: Incubation time
- 1.2: The correction value based upon the difference in dilution of the test sample and the standard solution.

Alternatively, the lecithin substrate (0.3 ml) is added to a test tube A and thereto is added a test sample (a blood serum or plasma, 0.5 ml) and they are mixed well. Separately, to test tubes B and C is added 20 mM sodium cholate (each about 0.05 ml). The content (0.2 ml) of the test tube A is added to the test tube B and it is allowed to stand at room temperature. Besides, the test tube A is incubated at 37° C for 2 hours and then the content (0.2 ml) of the test tube A is added to the test tube C. To the test tubes B and C is added the same reagent for measuring the free cholesterol as mentioned above (each 3 ml) and then they are incubated at 37° C for 20 minutes. Thereafter, the optical density at 500 nm of the resulting mixture is measured. Separately, the optical density of the standard solution containing a constant concentration of the free cholesterol is measured. On the basis of the values thus measured, the activity of LCAT is calculated by the following equation.

$$U = \frac{(E_B - E_C)}{E_S} \times D \times \frac{1}{T} \times 1.6 \quad [II]$$

wherein
- $U$: Unit of the activity of LCAT (μM/l/hour)
- $E_B$: The optical density of the test sample in the test tube B
- $E_C$: The optical density of the test sample in the test tube C
- $E_S$: The optical density of the standard solution
- $D$: The concentration of the free cholesterol of the standard solution (μM/l)
- $T$: Incubation time
- 1.6: The correction value based upon the difference in dilution of the test sample and the standard solution.

The present invention is illustrated by the following Examples but is not limited thereto.

EXAMPLE 1

A. Preparation of the lecithin substrate

To dipalmitoyl-lecithin (0.25 – 0.5 g) are added TEN buffer solution (pH 7.4, 50 ml) and Nonion NS 215 (0.1 – 0.5 g) and they are mixed well. The mixture is heated at about 50° C for 5 to 20 minutes to dissolve them. After cooling, to the mixture is added TEN buffer solution so as to make totally 100 ml.

B. Preparation of a coloring agent

Peroxidase (100 units), phenol (200 mg) and 4-aminoantipyrine (20 mg) are dissolved in a 0.1 M phosphate buffer solution (pH 6.7) containing 0.05% (W/V) of Triton X-100 so as to make totally 100 ml.

C. Preparation of the enzyme solution

Cholesterol oxidase (50 – 100 units) is dissolved in a 0.1 M phosphate buffer solution (pH 6.7) containing 0.1% (W/V) of Triton X-100 so as to make totally 100 ml.

D. Preparation of the reagent for measuring the free cholesterol

The coloring agent and the enzyme solution are mixed in the ratio of 2 : 1 by volume.

E. The measurement of the activity of LCAT

A blood serum (each 0.5 ml) is added to two test tubes A and B and thereto is added the lecithin substrate (each 0.1 ml). The test tube A is kept in a refrigerator. The test tube B is incubated at 37° C for 3 hours. The test sample (each 0.1 ml) of the test tubes A and B is taken out therefrom and thereto is added the reagent for measuring the free cholesterol (each 3 ml). The resulting mixture is kept at 37° C for 30 minutes. The optical density of the mixtures is measured against a reagent blank. As the result, the test sample of the test tube A has an optical density of 0.287 and that of the test tube B has an optical density of 0.243.

Likewise, the optical density of the standard solution (the content of the free cholesterol: 50mg/100 ml) is measured. As the result, the optical density thereof is 0.312.

By the equation [I] as mentioned before, the activity of LCAT is calculated as 28 units (μg/ml/hour).

EXAMPLE 2

A. Preparation of the lecithin substrate

Dimyristoyl-lecithin (0.25 – 0.5 g), 0.1 M phosphate buffer solution (pH 7.4, 50 ml) and Emulgen 930 (0.2 – 0.3 g) are mixed well. The mixture is heated at about 50° C for 5 to 20 minutes to dissolve them. After cooling, 0.1 M phosphate buffer solution is added thereto so as to make totally 100 ml.

B. The measurement of the activity of LCAT

In the same manner as described in Example 1, the activity of LCAT is measured by using a blood serum (0.5 ml) and the lecithin substrate (0.1 ml). As the result, the optical density of the test sample of the test tube A is 0.251, that of the test sample of the test tube B is 0.221 and that of the standard solution (the content of the free cholesterol: 50 mg/100 ml) is 0.316, and the activity of LCAT is 19 units.

EXAMPLE 3

A. Preparation of the lecithin substrate

Distearyl-lecithin (0.25 – 0.5 g), 0.02 M tris buffer solution (pH 7.4, 50 ml) and Tween 80 (about 0.5 g) are mixed well. The mixture is heated at about 50° C for 5 to 20 minutes to dissolve them. After cooling, to the mixture is added 0.02 M Tris buffer solution so as to make totally 100 ml.

B. Preparation of the reagent for measuring the free cholesterol

Cholesterol oxidase (50 – 100 units), peroxidase (200 units), phenol (400 mg) and 4-aminoantipyrine (40 mg) are dissolved in a 0.1 M phosphate buffer solution (pH 6.7) containing 0.1% (W/V) of Triton X-100 so as to make totally 300 ml.

C. The measurement of the activity of LCAT

In the same manner as described in Example 1, the activity of LCAT is measured by using a blood serum (0.5 ml) and the lecithin substrate (0.1 ml). As the result, the optical density of the test sample of the test tube A is 0.261, that of the test sample of the test tube B is 0.223 and that of the standard solution (the content of the free cholesterol: 50 mg/100 ml) is 0.316, and the activity of LCAT is 24 units.

EXAMPLE 4

A. Preparation of the lecithin substrate

Dipalmitoyl-lecithin (0.5 – 1 g), TEN buffer solution (pH 7.4, 50 ml) and Triton X-100 (about 0.2 g) are mixed well. The mixture is heated at about 50° C for 5 to 20 minutes to dissolve them. After cooling, to the mixture is added TEN buffer solution so as to make totally 100 ml.

B. Preparation of the reagent for measuring the free cholesterol

Cholesterol oxidase (50 – 100 units), peroxidase (200 units), phenol (400 mg) and 4-aminoantipyrine (40 mg) are dissolved in a 0.1 M phosphate buffer solution (pH 6.7) containing 0.1% (W/V) of Triton X-100 so as to make totally 300 ml. The mixture is lyophilized. The lyophilized product is reconstituted with a distilled water so as to make totally 300 ml, when used.

C. The measurement of the activity of LCAT

In the same manner as described in Example 1, the activity of LCAT is measured by using a blood serum (0.5 ml) and the lecithin substrate (0.1 ml). As the result, the optical density of the test sample of the test tube A is 0.245, that of the test sample of the test tube B is 0.217 and that of the standard solution (the content of the free cholesterol: 50 mg/100 ml) is 0.314, and the activity of LCAT is 18 units.

EXAMPLE 5

A. Preparation of the lecithin substrate

To dimyristoyl-lecithin (0.25 – 0.5 g) is added TEN buffer solution (pH 7.4, 50 ml) and the mixture is treated with an ultrasonic, and thereto is added Nonion NS 215 (0.1 – 0.5 g) and they are mixed well to dissolve them. To the mixture is added TEN buffer solution so as to make totally 100 ml.

B. The measurement of the activity of LCAT

In the same manner as described in Example 1, the activity of LCAT is measured by using a blood serum (0.5 ml) and the lecithin substrate (0.1 ml). As the result, the optical density of the test sample of the test tube A is 0.241, that of the test sample of the test tube B is 0.219 and that of the standard solution (the content of the cholesterol: 50 mg/100 ml) is 0.313, and the activity of LCAT is 14 units.

EXAMPLE 6

A blood serum (each 0.5 ml) is added to two test tubes A and B and thereto is added any one of the lecithin substrates prepared in Examples 1 to 5 (each 0.1 ml). To the test tube A is added 20 mM sodium cholate (0.05 ml) and it is allowed to stand at room temperature. The test tube B is incubated at 37° C for 3 hours. The test sample (each 0.1 ml) of the test tubes A and B is taken out therefrom and thereto is added the reagent for measuring the free cholesterol (each 3 ml) and the mixture is heated at 37° C for 30 minutes. The optical density of the mixture is measured against a reagent blank. As the result, the optical density of the test sample of the test tube A is 0.263, that of the test sample of the test tube B is 0.230 and that of the standard solution (the content of the free cholesterol: 50 mg/100 ml) is 0.319, and the activity of LCAT is 21 units.

EXAMPLE 7

A. Preparation of the lecithin substrate

To distearyl-lecithin (0.25 g) is added TE buffer solution (Tris: 0.02 M, EDTA: 0.001 M, pH 7.4, 30 ml), and the mixture is treated with an ultrasonic and thereto is added Tween 20 (0.025 g). After mixing well, to the mixture is added TE buffer solution so as to make totally 100 ml.

B. The measurement of the activity of LCAT

The lecithin substrate (0.3 ml) is added to test tube A and thereto is added a blood serum (0.5 ml) and they are mixed well. Separately, a 20 mM sodium cholate (each about 0.05 ml) is added to two test tubes B and C. To the test tube B is added the content (0.2 ml) of the test tube A and it is allowed to stand at room temperature. The mixture of the test tube A is incubated at 37° C for 2 hours, and then the content thereof (0.2 ml) is added to the test tube C. To the test tubes B and C is added the reagent for measuring the free cholesterol (each 3 ml) and they are incubated at 37° C for 20 minutes. The optical density at 500 nm of these test samples is measured against a reagent blank. As the result, the optical density of the test sample of the test tube B is 0.384 and that of the test sample of the test tube C is 0.352.

Likewise, the optical density of the standard solution (the content of the free cholesterol: 1,000 $\mu$M/liter) is measured. As the result, the optical density of the standard solution is 0.377.

By the equation [II] as mentioned before, the activity of LCAT is calculated as 68 units ($\mu$M/l/hour).

EXAMPLE 8

A. Preparation of the lecithin substrate

To dipalmitoyl-lecithin (0.25 g) is added TE buffer solution (30 ml) and the mixture is treated with an ultrasonic, and thereto is added Triton X-100 (0.025 g) and they are mixed well to dissolve them. To the mixture is added TE buffer solution so as to make totally 100 ml.

B. The measurement of the activity of LCAT

In the same manner as described in Example 7, the activity of LCAT is measured by using a blood serum (0.5 ml) and the lecithin substrate (0.3 ml). As the result, the optical density of the test sample of the test tube B is 0.350, that of the test sample of the test tube C is 0.308 and that of the standard solution (the content of the free cholesterol: 1,000 μM/liter) is 0.379, and the activity of the LCAT is 89 units.

Thus, according to the present invention, the activity of LCAT can be easily measured by a conventional optical analysis method without using any radioisotope, and therefore, the method of the present invention is useful for the clinical test for the liver function of patients and further for the diagnosis of the diseases, such as lipidosis and diabetes.

What is claimed is:

1. A method for measuring the activity of lecithin cholesterol acyl transferase, which comprises adding a test sample to a lecithin substrate solution containing a lecithin and a nonionic surfactant, incubating the mixture and then measuring the changed amount of the free cholesterol in the reaction system by an optical analysis.

2. The method according to claim 1, wherein the lecithin substrate solution comprises 2.5 to 10 mg/ml of a lecithin and 0.01% (W/V) or more of a nonionic surfactant in a buffer solution.

3. The method according to claim 2, wherein the nonionic surfactant is contained in an amount of 0.02 to 0.5% (W/V) on the basis of the lecithin substrate solution.

4. The method according to claim 2, wherein the lecithin is contained in an amount of 2.5 to 5 mg/ml.

5. The method according to claim 1, wherein the incubation is carried out at about 37° C for 2 to 4 hours.

6. The method according to claim 1, wherein the measurement of the optical density is carried out at 500 nm.

7. A lecithin substrate solution for the measurement of the activity of lecithin cholesterol acyl transferase, comprising 2.5 to 10 mg/ml of a lecithin and 0.01% (W/V) or more of a nonionic surfactant in a buffer solution.

8. The lecithin substrate solution according to claim 7, wherein the nonionic surfactant is contained in an amount of 0.02 to 0.5% (W/V) on the basis of the lecithin substrate solution.

9. The lecithin substrate solution according to claim 7, wherein the lecithin is contained in an amount of 2.5 to 5 mg/ml.

10. The lecithin substrate solution according to claim 7, wherein the buffer solution is a member selected from the group consisting of TEN buffer solution, TE buffer solution, 0.1 M phosphate buffer and 0.02 M Tris buffer solution.

* * * * *